United States Patent [19]

Nakayama et al.

[11] Patent Number: 4,804,329

[45] Date of Patent: Feb. 14, 1989

[54] CONNECTING DEVICE FOR AN ILLUMINANT HANDPIECE

[75] Inventors: Shozo Nakayama, Muko; Shinichiro Madenokoji, Yahata, both of Japan

[73] Assignee: Kabushiki Kaisha Morita Seisakusho, Kyoto, Japan

[21] Appl. No.: 50,538

[22] Filed: May 14, 1987

[30] Foreign Application Priority Data

May 16, 1986 [JP] Japan .............................. 61-74476[U]

[51] Int. Cl.⁴ ............................................ H01R 39/02
[52] U.S. Cl. ...................................... 439/20; 439/191; 433/103
[58] Field of Search ...................... 439/11, 18, 20, 190, 439/194, 481; 433/25, 103; 362/119

[56] References Cited

U.S. PATENT DOCUMENTS 3,590,232 6/1971 Sadowski .......................... 362/119 X
3,614,414 10/1971 Gores ............................... 362/119 X
4,642,738 2/1987 Meuer ................................. 362/119

*Primary Examiner*—Eugene F. Desmond
*Attorney, Agent, or Firm*—Koda and Androlia

[57] ABSTRACT

A connecting means for an illuminant handpiece being characterized in that the connecting device is adapted such that at least one of the electrical connections of the electric power receiving terminals of the illumination lamp and the electric power supply terminals is performed by fitting at a position close to the axis of the grip section almost symmetrically about the axis, and the other electrical connection is performed by fitting almost symmetrically about the axis or by abutting co-axially about the axis so as to permit a mutual rotation of the terminals. With this structure, the diameter of the connection area can be made small and the grip section can have an easy-to-hold size. In addition, the distance to the irradiation section can be reduced and efficient irradiation with less optical loss is obtained. Moreover, the space or lamp replacement can be reduced.

4 Claims, 2 Drawing Sheets

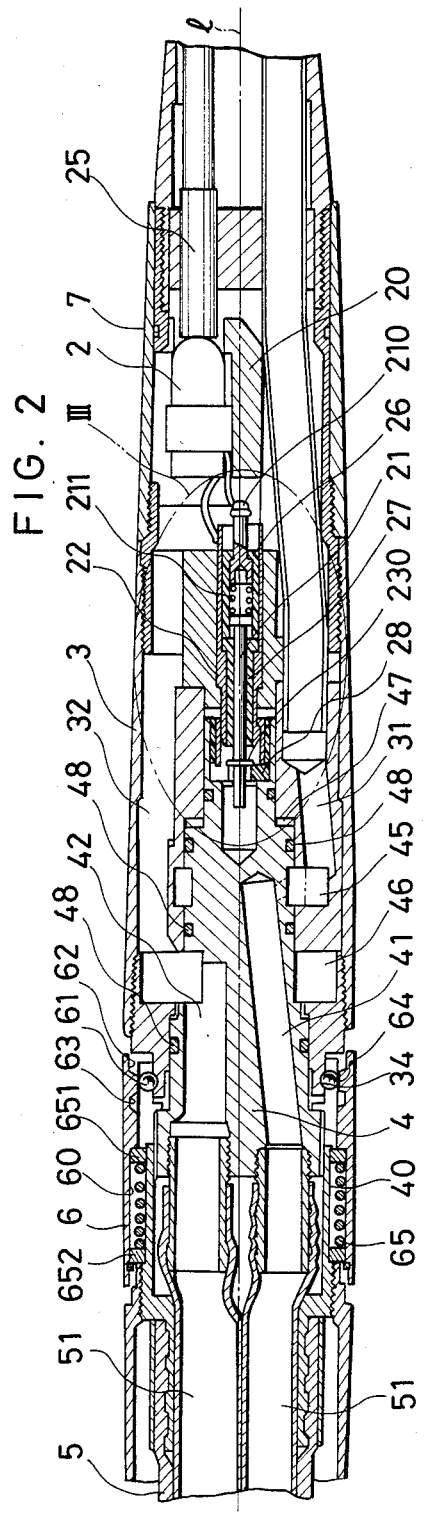

CONNECTING DEVICE FOR AN ILLUMINANT HANDPIECE

BACKGROUND OF THE INVENTION

1. Field of the Invention

The present invention relates to a connecting device for an illuminant handpiece mainly used for dental treatment

2. Prior Art

The cutting tool installed in the head of a dental handpiece is driven pneumatically or electrically. The drive force thus obtained is used to cut defective portions of teeth for treatment. Passages for a medium used to rotate the cutting tool are built in the grip section of the handpiece. In parallel with these passages, the passages for activation media such as water and air used to cool the rotation section of the handpiece or to remove tooth chips are also provided in some handpieces. These drive and activation media are supplied from the connection block provided at the rear end of the grip section. The supply pipes and/or flexible hose accommodating a bundle of conductors used to supply the above-mentioned media are connected to the connection block The connection between the grip section and the connection block is rotatable so that the flexible hose is not twisted during use and so that the grip can be used smoothly with little resistance. Furthermore, the connection is made separable. To ensure proper connection at this connection section, the means for connecting the passages of the above-mentioned drive and activation media has been invented in various types. In addition, an illumination means to light treatment portions has been provided recently for the handpiece equipped with the above-mentioned rotatable grip section to ensure higher convenience during dental treatment. As the above-mentioned illumination means, the following three methods have been practically used. (1) A method of transmitting light from a light source outside the handpiece to the head of the handpiece via a photoconductive substance (2) A method of transmitting light to the head by coaxially providing an illumination lamp on the connection surface of the connection block, by building in a photoconductive substance in the grip section and by facing the rear end of the photoconductive substance to the lamp. (3) A method of irradiating light from the head section via a photoconductive substance provided in the grip section by providing the illumination lamp in the grip section and by rotatably connecting the terminals of the lamp at a connection section of a connection block. (Problems to be solved by the invention) The above-mentioned illumination methods have the following defects. In the case of method (1), the flexibility of the connection tube is deteriorated since the photoconductive substance is built in the connection tube. In the case of method (2), the illumination lamp must be disposed at the center of the handpiece. Therefore, it is very difficult to properly allocate the space for lamp replacement and the space for the passages for the activation media, resulting in a larger pipe diameter at the connection section. In the case of method (3), the loss is small and the lamp can be easily replaced since the lamp can be disposed close to the external circumference of the handpiece. In addition, it is relatively easy to allocate space for lamp replacement and space for the passages. However, at the connection section between the grip section and the connection block, what is called a slip joint, wherein one of two terminals provided in the thrust direction is slidably contacted by the other terminal in the radial direction, is used to electrically connect the power supply terminals and the lamp terminals Due to this structure of the slip joint, it is inevitable that the connection section becomes larger in diameter. Accordingly, none of the above-mentioned methods is satisfactory in terms of structure or handling.

SUMMARY OF THE INVENTION

It is therefore an object of the present invention to provide a novel and easy-to-handle connecting device for an illuminant handpiece wherein light from an illumination lamp is effectively irradiated to desired portions, the electric power supply wires for the illumination lamp are rotatably connected and the passages for various media are also rotatably connected within a compact area

BRIEF DESCRIPTION OF THE DRAWINGS

FIG. 2 is a horizontal partially-sectional top view of the embodiment; and

FIG. 3 is an enlarged broken perspective view taken on line III of FIG. 2.

DETAILED DESCRIPTION OF THE INVENTION

Figure 1:
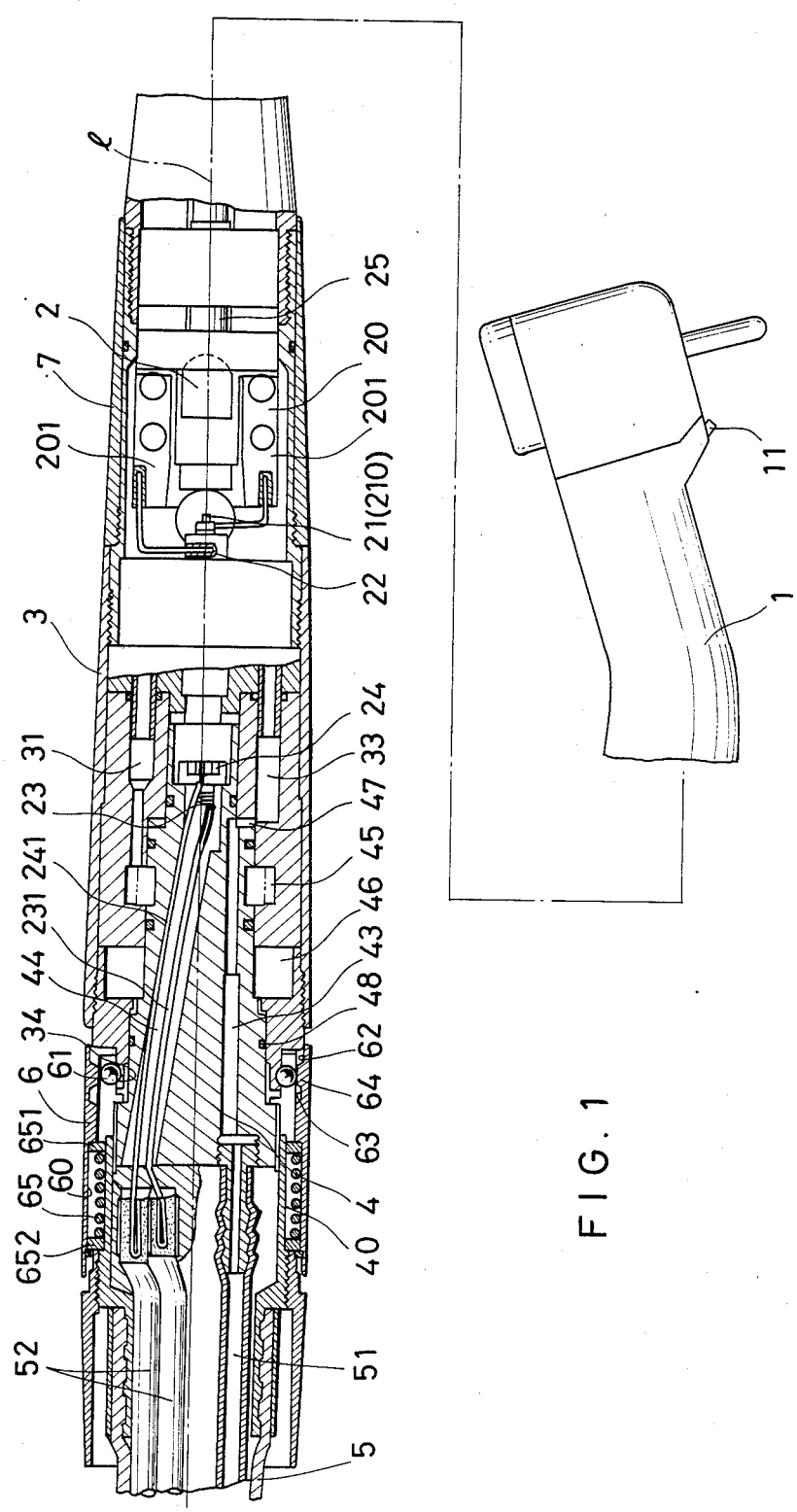
FIG. 1 is a vertical partially-sectional front view illustrating an embodiment of the handpiece employing the mechanism of the present invention.

The device shown in FIGS. 1, 2 and 3 is a basic embodiment of the present invention. The connecting device for the illuminant handpiece of the present invention comprises a head section 1 provided at the front end of the handpiece, a grip section 3 extended to the head section 1, an illumination lamp 2 built in the grip section 3 to irradiate light from the head section 1, passages 31, 32, and 33 built in the grip section 3 to flow working media such as water and air, and a connection block 4 which includes electric power supply terminals 23 and 24 and passages 41, 42, 43 and 44 for activation media, and is connected to the rear end of the grip section 3. More specifically the connecting device is adapted such that at least one of the electrical connections of the electric power receiving terminals 21 and 22 of the illumination lamp 2 and the electric power supply terminals 23 and 24 is performed by fitting at a position close to the axis 1 of the grip section 3 almost symmetrically about the axis 1, and the other electrical connection is performed by fitting almost symmetrically about the axis 1 or by abutting coaxially about the axis 1 so as to permit a mutual rotation of the electric power receiving terminals 21 and 22 and the electric power supply terminals 23 and 24 around the axis 1 while maintaining both of the electrical connections. A contra-angle type air turbine handpiece to which the connecting device of the invention is applied is shown in FIGS. 1, 2 and 3. To the rear end of the connection block 4, a flexible hose 5 including a bundle of supply pipes 51 for various working media and electrical wires 52 is connected. The supply pipes 51 and electrical wires 52 are flexible in themselves. In particular, the electrical wires 52 which are highly elastic and are not easily broken even when the hose 5 is deformed or bent due to sliding, are preferably employed. The connection block 4 includes an air supply passage 41 used to drive the air turbine built in the head section 1, an exhaust passage 42, water supply passage 43 and a passage 44 which accommodates the lead wires 231 and 241 connected to the electric power supply terminals 23 and 24. These passages 41, 42 and 43 are connected to the supply pipes 51 in the flexible hose 5. The lead wires 231 and 241 are connected to the electrical wires 52. The passage 44 accommodating the lead wires 231 and 241 is extended to the central section at the front end of the connection block 4. Also at the front end, the electric power supply terminals 23 and 24 are provided and the lead wires 231 and 241 are abutted to the terminals 23 and 24 respectively. The connection section of the connection block, connected to the grip section 3 is coaxially enlarged in diameter step by step from the portion wherein the electric power supply terminals 23 and 24 are formed to the rear end. The ends of the passages 41, 42 and 43 are open at the corresponding steps. The connection section of the grip section 3, connected to the connection block 4, has steps formed coaxially to removably accommodate the step-formed connection section of the connection block 4. At the central section of the connection section of the grip section 3, the electric power receiving terminals 21 and 22 for the lamp are provided. The rear ends of the passages 31, 32 and 33 of the connection section are open at the steps corresponding to the passages 41, 42 and 43. The passages 31, 32 and 33 are respectively connected to the passages 41, 42 and 43 via circumferential grooves 45, 46 and 47 air-tightly or water-tightly This air tightness or water-tightness is attained by the 0-rings 48 provided around the step-formed connection section of the connection block 4 Some portions of the exhaust passage 32 of the grip section 3 are formed by the space between the casing of the grip section 3 and the various members built in the casing and thus cannot be illustrated clearly in the attached figures. The grip section 3 and the connection block 4 are rotatably connected by the step-formed fitting structure formed coaxially as described above. The locking of the rotatable connection and separation are attained by the lock ring 6 fitted over the circumference of the connection block 4 and being slidable back and forth in the longitudinal direction of the handpiece, by a plurality of lock balls 61 being held inside the lock ring 6 so that the lock balls 61 can move in the radial direction of the connection block 4, and by the circumferential groove 34 formed around the external circumference at the rear end of the grip section 3. More particularly, two circumferential grooves 62 and 63 are formed on the internal surface at the front end of the lock ring 6, and a circumferential projection 64 is formed between the circumferential grooves 62 and 63. In addition, a compression spring 65 is resiliently installed between the rear internal surface of the lock ring 6 and the external circumference of the connection block 4. Normally, the circumferential projection 64 is positioned just above the lock ball 61 by the resilience of the compression spring 65 to prevent the lock ball 61 from moving in the radial direction. Both ends of the compression spring 65 are secured by spring supports 651 and 652 which are slidable to both the lock ring 6 and the connection block 4. The compression spring 65 is resiliently installed in the space comprising two mating concave areas: the concave area 60 formed around the internal circumference Of the lock ring 6 and the concave area 40 formed in the external circumference of the connection block 4. When the circumferential projection 64 abuts the lock ball 61, the lock ball 61 fits in the circumferential groove 34 and is prevented from moving out of the groove 34. As a result, the grip section 3 and the connection block 4 are rotatably connected When the lock ring 6 is moved back or forth against the resilience of the compression spring 65, the abutting contact of the circumferential projection 64 to the lock ball 61 is canceled. Since the circumferential groove 62 or 63 is provided in the radial direction of the lock ball 61 at this time, the lock ball 61 can move out in the radial direction (can move out of the circumferential groove 34). Therefore, the grip section 3 can be separated from the connection block 4. An illumination lamp socket 20 is built in the grip section 3 and the lamp 2 is replaceably installed in the socket 20 A pair of electrodes 201, 201 of the socket 20 are connected to the electric power receiving terminals 21 and 22. The socket 20 is eccentrically installed in the grip section 3, contacting the circumferential wall of the grip section 3 At the installation position of the socket 20, a lamp replacement sleeve cover 7 is screwed into the grip section 3 from the head section 1. When the cover 7 is loosened and moved to the head section 1, the lamp 2 can be replaced from the outside of the grip section 3. The rear end of the photoconductive substance 25 leading to the irradiation section 11 provided in the head section 1 faces the front surface of the lamp 2 installed in the socket 20. Light passes from the lamp 2 to the irradiation section 11 via the photoconductive substance 25 and is irradiated to a treatment portion.

The electric power receiving terminals 21 and 22 and the electric power supply terminals 23 and 24 are electrically connected as described below. At the center of the grip section 3, a terminal base section 210 is secured coaxially about the axis 1 of the grip section 3. An electric power receiving terminal 21 is resiliently biased to the connection block side by a compression spring 211 to be electrically connected to the end f the base section 210 on the connection block side. Over the electric power receiving terminal 21, the compression spring 211 and the terminal base section 210, the other electric power receiving terminal 22, having a shape of a small-diameter cylinder, is fitted via support members 26 and 27 made of electrically insulating resin. On the connection block side of the electric power receiving terminal 22, slits 221 are formed in parallel with the axis 1. The terminal 22 and the terminal base section 210 are connected to the electrodes 201, 201 of the socket 20 respectively The electric power receiving terminal 21 is slidable back and forth on the surfaces of the support members 26 and 27 along the axis 1 and is always resiliently biased by the compression spring 211 to the connection block 4 side. In the central section at the front end of the connection block 4, an electric power supply terminal 23 is secured. The terminal 23 has a disc-shaped terminal surface 230 to resiliently contact the terminal 21. The other power supply terminal 24, having a shape of a cylinder, coaxially encloses the terminal 23 via a support member 28 made of insulating resin to ensure electrical insulation. In this way, the electric power supply terminals 23 and 24 are connected to the leads 231 and 241 respectively. When the grip section 3 is connected to the connection block 4, the electric power supply terminal 23 resiliently contacts the electric power receiving terminal 21. The electric power supply terminal 24 fits over the electric power receiving terminal 22. As a result, rotatable electrical connections are obtained. The connection between the terminals 21 and 23 can also be made by coaxial fitting in the same way as the connection between the terminals 22 and 24. With the connecting device of the illuminant handpiece having the structure described above, the rotatable connection between the grip section 3 and the connection block 4 is maintained when the lock ring 6 is not operated Therefore, the flexible hose 5 connected to the rear end of the connection block 4 is not twisted and less resistance is caused when the grip section 3 is held during dental treatment. The passages 31, 32, and 33 and 41, 42, 43 and 44 for drive and working media such as water and air are rotatably communicated with each other. By the working of the media supplied through these passages, the intended function of the handpiece can be performed at the held section 1. Among the connection terminals used to supply electric power to the lamp 2, the electric power receiving terminal 21 and the electric power supply terminal 23 are connected by coaxial resilient abutting along the axis 1 as described above. The other pair of terminals: the electric power receiving terminal 22 and the electric power supply terminal 24, are connected by fitting the the two cylindrical members coaxially about the axis 1. Therefore, these terminals are electrically connected rotatably. In the case that at the end of the electric power receiving terminal 22, the slits 221 are formed in parallel with the axis 1 as shown in the attached figures, the resilience of the terminal pieces separated by slits 221 may maintain proper contact condition at all times even when these terminals have a slight out-of-roundness. In addition, in the case that the electric power receiving terminal 21 resiliently abuts the disc-shaped terminal surface 230 provided at the front end of the electric power supply terminal 23, the contact section of the terminal 21 has a high degree of freedom in the plane of the disc-shaped terminal surface 230 (electrical connection is obtained regardless of the contact position in the plane). Therefore, proper contact condition is maintained even when these terminals have a slight out-of-roundness. The connection sections of these terminals can thus be made extremely compact Accordingly, the diameter of the electrical connection area can be made small in diameter and the external diameter of the grip section 3 can be reduced to an easy-to-hold size. Furthermore, since the lamp 2 is built in the grip section 3, the lamp 2 is not affected by the rotatably connection. The optical axis of the lamp 2 is thus not necessary to be aligned with the axis 1. The lamp 2 can be disposed close to the external wall of the grip section 3 so that the lamp 2 can be easily replaced The problem of space allocation for the lamp 2 and the passages 31, 32 and 33 can be solved relatively easily. Since the lamp 2 is disposed close to the head section 1, the distance from the lamp 2 to the irradiation section can be reduced to ensure efficient irradiation with less optical loss. As described above, with the connecting device for an illuminant handpiece of the present invention, the terminals 21, 22, 23 and 24 are electrically connected by resilient abutting along the axis 1 and/or by coaxial fitting close to the axis 1 to supply electric power to the illumination lamp 2. The diameter of the electrical connection area can be made small The grip section 3 can thus be made to an easy-to-hold size. Since the lamp 2 is built in the grip section 3, the distance from the lamp 2 to the irradiation section can be reduced and efficient irradiation with less optical loss is obtained. Moreover, since the illumination lamp 2 can be eccentrical about the axis 1, the space for lamp replacement can be reduced. Therefore, the lamp 2 and the passages for activation media 31, 32 and 33 can be easily allocated. This is advantageous in design of handpieces. The connecting device, wherein the terminals 21, 22, 23 and 24 are rotatably connected, and the passages 31, 32, and 33 and 41, 42, 43 and 44 are also rotatably connected, is not limited to the embodiment of the present invention but can be changed variously within the spirit of the present invention.

We claim:

1. A connecting device for an illuminated handpiece comprising a head section provided at the front end of said handpiece, a grip section extended to said head section, an illumination lamp built in said grip section to irradiate light from said head section via an irradiation section, passages built in said grip section to flow working media such as water and air, and a connecting block which includes electric power supply terminals, and passages for working media, and is connected to the rear end of said grip section, characterized in that said connecting device is adapted such that at least one of two electrical connections of electric power receiving terminals of said illumination lamp and of said electric power supply terminals is performed by fitting at a position close to the axis of said grip section almost symmetrically about said axis, and an other of the two electrical connections of the electric power receiving terminals and of the electric power supply terminals is performed by abutting coaxially about said axis so as to permit a mutual rotation of said electric power receiving terminals and said electric power supply terminals around said axis while maintaining both of said electrical connections.

2. A connecting device according to claim 1, wherein said other electric power receiving terminal is resiliently abutted to said electric power supply terminal by the force of a compression spring provided coaxially about said axis, and said one electric power receiving terminal is inserted in said electric power supply terminal which is cylindrical coaxially about said axis.

3. A connecting device according to claim 2, wherein a plurality of slits are formed on the cylindrical wall of said one electric power receiving terminal in parallel with said axis.

4. A connecting device according to claim 1, wherein said grip section and said connection block are connected via a lock ring so that said grip section and said connection block can be rotatably connected and disconnected by operating said lock ring.

* * * * *